United States Patent
Schoenfuss et al.

(10) Patent No.: US 12,180,445 B2
(45) Date of Patent: Dec. 31, 2024

(54) DEVICE FOR MONITORING A BIOLOGICAL PROCESS IN A LIQUID MEDIUM

(71) Applicant: Hamilton Bonaduz AG, Bonaduz (CH)

(72) Inventors: Dirk Schoenfuss, Tamins (CH); Frederic Juillerat, Paspels (CH)

(73) Assignee: Hamilton Bonaduz AG, Bonaduz (CH)

( * ) Notice: Subject to any disclaimer, the term of this patent is extended or adjusted under 35 U.S.C. 154(b) by 886 days.

(21) Appl. No.: 17/151,158

(22) Filed: Jan. 16, 2021

(65) Prior Publication Data

US 2021/0147776 A1    May 20, 2021

Related U.S. Application Data

(63) Continuation-in-part of application No. PCT/EP2019/068437, filed on Jul. 9, 2019.

(30) Foreign Application Priority Data

Jul. 18, 2018 (DE) .......................... 102018117332.6
Jul. 9, 2019 (WO) .................. PCT/EP2019/068437

(51) Int. Cl.
*C12M 1/00* (2006.01)

(52) U.S. Cl.
CPC ............ *C12M 23/14* (2013.01); *C12M 23/20* (2013.01); *C12M 23/26* (2013.01); *C12M 23/28* (2013.01); *C12M 29/18* (2013.01)

(58) Field of Classification Search
CPC ...... C12M 23/14; C12M 23/20; C12M 23/26; C12M 23/28; C12M 29/18; C12M 1/3407; C12M 41/36; C12M 41/46; G01N 27/221
See application file for complete search history.

(56) References Cited

U.S. PATENT DOCUMENTS

| 7,323,887 B2 * | 1/2008 | Feng ................... C25D 17/02 73/54.01 |
| 2006/0189788 A1 | 8/2006 | Araki et al. ........... C08G 65/34 528/425 |

(Continued)

FOREIGN PATENT DOCUMENTS

| EP | 2503320 A2 * | 9/2012 | .............. C12M 1/00 |
| FR | 2812725 B1 | 4/2000 | |

(Continued)

OTHER PUBLICATIONS

Office action of the Chinese Patent Office in the related Chinese patent application CN201980050459.3 dated Nov. 21, 2023 (7 pages).

(Continued)

*Primary Examiner* — Elizabeth A Robinson
*Assistant Examiner* — Jonathan E Lepage
(74) *Attorney, Agent, or Firm* — Imperium Patent Works; Darien K. Wallace

(57) ABSTRACT

A device for monitoring a biological process in a liquid medium includes a wall portion, a silanization layer and a sensor arrangement. The device attaches to a container of a bioreactor and can be used with disposable bioreactors. The wall portion is adapted to retain the liquid medium during operation of the bioreactor. A through-hole is disposed in the wall portion. A silanization layer covers the surface encircling the through-hole and the wall portion between the liquid medium and the wall portion. The sensor arrangement includes a glass layer, a substrate and an electrode. The glass layer is bonded by an adhesive to the silanization layer so as to cover the through-hole. The electrode is mounted on the substrate and measures electrical conductivity through the liquid medium. The sensor arrangement also includes an (Continued)

optical sensor that detects electromagnetic radiation that passes from the liquid medium through the glass layer.

23 Claims, 10 Drawing Sheets

(56) References Cited

U.S. PATENT DOCUMENTS

| | | | |
|---|---|---|---|
| 2006/0219564 A1 | 10/2006 | Feng | C25D 21/12 |
| | | | 205/81 |
| 2011/0187388 A1 | 8/2011 | Ossart | G01R 27/28 |
| | | | 324/649 |
| 2014/0322786 A1 | 10/2014 | Deubel et al. | C08F 265/06 |
| | | | 435/180 |
| 2018/0002653 A1 | 1/2018 | Kaisermayer | C12M 1/12 |

FOREIGN PATENT DOCUMENTS

| | | | | |
|---|---|---|---|---|
| FR | 2867279 B1 | 3/2004 | | |
| FR | 2951547 A1 * | 4/2011 | | C12M 41/36 |
| WO | WO-03093406 A2 * | 11/2003 | | B01F 13/0059 |
| WO | WO-2004092235 A1 * | 7/2006 | | C08F 234/02 |

OTHER PUBLICATIONS

English translation of Office action of the Chinese Patent Office in the related Chinese patent application CN201980050459.3 dated Nov. 21, 2023 (3 pages).

\* cited by examiner

DEVICE FOR MONITORING A BIOLOGICAL PROCESS IN A LIQUID MEDIUM

CROSS REFERENCE TO RELATED APPLICATION

This application is filed under 35 U.S.C. § 111(a) and is based on and hereby claims priority under 35 U.S.C. § 120 and § 365(c) from International Application No. PCT/EP2019/068437, filed on Jul. 9, 2019, and published as WO 2020/016064 A1 on Jan. 23, 2020, which in turn claims priority from German Application No. 102018117332.6, filed in Germany on Jul. 18, 2018. This application is a continuation-in-part of International Application No. PCT/EP2019/068437, which is a continuation of German Application No. 102018117332.6. International Application No. PCT/EP2019/068437 is pending as of the filing date of this application, and the United States is an elected state in International Application No. PCT/EP2019/068437. This application claims the benefit under 35 U.S.C. § 119 from German Application No. 102018117332.6. The disclosure of each of the foregoing documents is incorporated herein by reference.

TECHNICAL FIELD

The invention relates to a device for monitoring a biological process in a liquid medium. The invention further relates to a bioreactor having a container and a monitoring device according to the invention. The invention further relates to a method for producing a device for monitoring a biological process in a liquid medium.

BACKGROUND

The cultivation of biomass in a bioreactor, that is also referred to as a fermenter, requires constant monitoring of the parameters prevalent in the bioreactor, such as, for example, the cell density, the oxygen content or the pH value. For monitoring these parameters and other parameters, the bioreactors are provided with corresponding sensors that project into the bioreactor.

Biomass is cultivated increasingly in pre-sterilized disposable bioreactors made of flexible plastic material. The circulation of the biomass during operation of the bioreactor is achieved by moving a container made of the flexible plastic material, for example, by means of a rocker device.

Because of the structure and associated operating, storage and sterilization conditions of the disposable bioreactors, the associated sensor arrangements must be differently constructed than the sensors of conventional steel fermenters. The sensor arrangements should be cost-effective to produce because they can be used only once, while they should be at least as good as those of conventional fermenters in relation to measurement accuracy and stability. Examples of the sensors are inter alia known for optical pH or oxygen measurement. Furthermore, sensors having electrodes for the electrochemical/capacitive biomass or cell density measurement are known. For example, metal wires are used as electrodes.

The sensor arrangements are generally fixedly installed from the beginning in the disposable bioreactor and have to withstand the movements of the bioreactor during operation of the bioreactor. Furthermore, the sensor arrangements have to be fitted to the bioreactor in such a manner that neither gases nor liquids can be discharged from the bioreactor.

In order to be cost-effective to produce, the sensor arrangements for the disposable bioreactors are also intended to have a simple construction type.

Therefore, there is a need for sensor arrangements that are suitable for disposable bioreactors and that have a simple construction type.

SUMMARY

A device for monitoring a biological process in a liquid medium includes a wall portion, a silanization layer, a sensor arrangement and an adhesive. The monitoring device is attached to a container of a bioreactor and can be used with flexible, disposable bioreactors. The wall portion is adapted to retain the liquid medium during operation of the bioreactor. A through-hole is disposed in the wall portion of the monitoring device. A silanization layer covers the surface encircling the through-hole and the wall portion between the liquid medium and the wall portion. The sensor arrangement includes a glass layer, a substrate and an electrode. The glass layer is bonded by an adhesive to the silanization layer so as to cover the through-hole. The electrode is mounted on the substrate and is adapted to measure electrical conductivity through the liquid medium. The sensor arrangement also includes an optical sensor that detects electromagnetic radiation that passes from the liquid medium through the glass layer and through-hole.

The present invention relates to a device for monitoring a biological process in a liquid medium, having a wall portion that is configured to retain the medium during operation of the device, a silanization layer, an adhesive and a sensor arrangement, wherein the wall portion has a through-hole. The silanization layer is applied directly to the wall portion and completely around the through-hole. The sensor arrangement has a carrier that has a glass layer. The adhesive sealingly bonds the silanization layer to the glass layer.

The invention further relates to a bioreactor having a device according to the invention and a container, in which the medium is intended to be arranged during bioreactor operation of the bioreactor, wherein the container has the wall portion, and wherein the biological process is intended to be carried out during the bioreactor operation.

The invention further relates to a method of producing a device for monitoring a biological process in a liquid medium, the method comprising the following steps:

a) providing a wall portion that is configured to retain the medium during operation of the device, and a silanization layer, wherein the wall portion has a through-hole, and the silanization layer is applied directly to the wall portion and completely around the through-hole;

b) providing a sensor arrangement, wherein the sensor arrangement has a carrier that has a glass layer;

c) tightly bonding the silanization layer to the glass layer by means of an adhesive; and d) curing the adhesive.

Other embodiments and advantages are described in the detailed description below. This summary does not purport to define the invention. The invention is defined by the claims.

BRIEF DESCRIPTION OF THE DRAWING

The accompanying drawings, where like numerals indicate like components, illustrate embodiments of the invention.

FIG. 2A shows a glass layer arranged between the electrodes and the substrate of the inventive device.

FIG. 2B shows a glass layer of the inventive device arranged between the electrodes and on a part-region on the surface of each electrode that faces away from the substrate, wherein the part-region completely contains the edge of the surface.

DETAILED DESCRIPTION

Reference will now be made in detail to some embodiments of the invention, examples of which are illustrated in the accompanying drawings.

Figure 1:
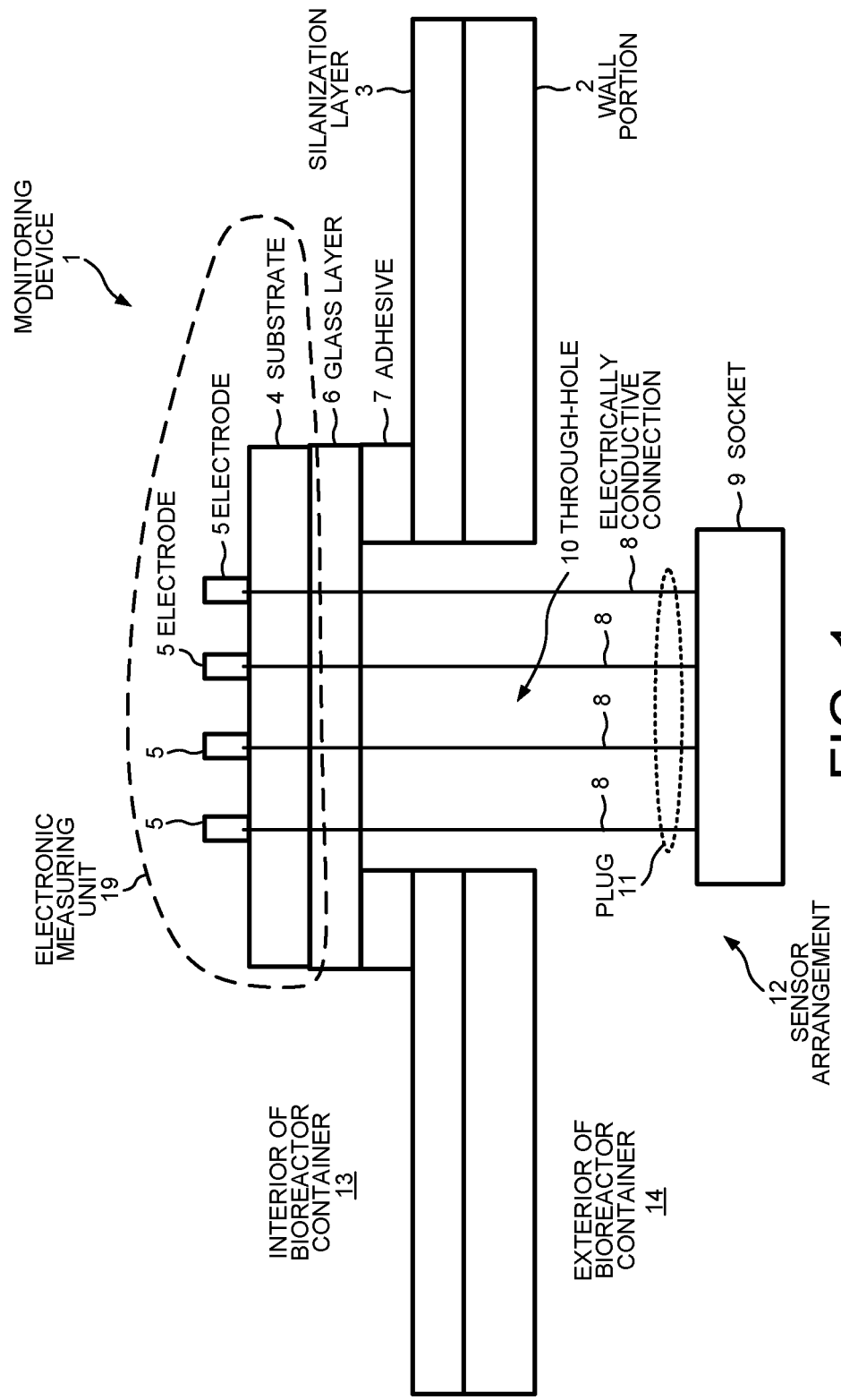
FIG. 1 is a schematic cross-section of an exemplary embodiment of the device according to the invention, wherein the substrate is fitted to a side of the wall portion that faces the interior of a bioreactor.

FIG. 1 shows a first aspect of the invention involving a device 1 for monitoring a biological process in a liquid medium. Monitoring device 1 has a wall portion 2 that is configured to retain the medium during operation of the device. The wall portion 2 has a through-hole 10. The device 1 also includes a silanization layer 3, an adhesive 7 and a sensor arrangement 12. The silanization layer 3 is applied directly to the wall portion 2 and completely around the through-hole 10. The sensor arrangement 12 includes a substrate 4, electrodes 5, a glass layer 6, electrically conductive connections 8 and a socket 9. The sensor arrangement 12 has a carrier that includes the glass layer 6. The glass layer 6 is applied directly to the substrate 4. The adhesive 7 tightly bonds the silanization layer 3 to the glass layer 6. The silanization layer 3, the adhesive 7 and the glass layer 6 are arranged completely around the through-hole 10. The electrodes 5 that are used for sensing are attached to the substrate 4. The electrodes 5 are coupled to the socket 9 via electrically conductive connections 8. The electrically conductive connections 8 may be metal pins that form a plug 11.

The device 1 is used to monitor a biological process in a liquid medium. The biological process may, for example, be the production of the biomass in a bioreactor. The liquid medium may, for example, be the nutritional medium of cells or bacteria that are being cultivated as the biomass in the bioreactor. The monitoring of the biological process is enabled by the sensor arrangement 12. Depending on the type of sensor used in the sensor arrangement 12, different parameters, such as, for example, cell density, oxygen content or pH value, can be detected and monitored.

The wall portion 2 of the device 1 is configured to retain the liquid medium during operation of the device. The wall portion 2 includes the through-hole 10 through which the monitored parameters can be output. To this end, for example, cables can be guided through the through-hole 10. Additionally or alternatively, it is conceivable for electromagnetic radiation carrying parameter information to be transmitted via the through-hole 10.

The device 1 also includes the silanization layer 3 that is fitted directly to the wall portion 2 and completely around the through-hole 10. The term "silanization" as used here is intended to be understood to refer to a chemical connection of a silane compound to a surface. The silanization layer 3 is formed by the silanization of the surface of the wall portion 2 and is applied directly to the wall portion 2 in this manner.

The device 1 further includes the sensor arrangement 12. The sensor arrangement 12 has the carrier, which has the glass layer 6. The glass layer 6 of the carrier provides a sealing face between the wall portion 2 and the carrier. The carrier further provides at least a portion of a technical measuring system of the sensor arrangement 12. For example, the carrier can carry the sensor and/or the carrier can be configured to allow the electromagnetic radiation to pass. In that the carrier provides the sealing face and a portion of the technical measuring system, the carrier is a component with two functions. The device thereby has a simple construction type.

The device also includes the adhesive 7. The adhesive 7 tightly bonds the silanization layer 3 to the glass layer 6. This means that the silanization layer 3 is adhesively bonded to the glass layer 6 in such a manner that the medium cannot pass the wall portion 2 via the through-hole 10. Therefore, the term "tightly" as used here is intended to be understood to mean liquid-tight. Preferably, the adhesive-bonding of the silanization layer 3 to the glass layer 6 is not only liquid-tight, but also air-tight. A prerequisite for the sealing achieved by the adhesive 7 is the combination of the glass layer 6, adhesive 7 and silanization layer 3. This material combination leads to the adhesive 7 both fixing securely and fixing tightly.

Since the adhesive 7 adhesively bonds the silanization layer 3 to the glass layer 6, and the silanization layer 3 is arranged completely around the through-hole 10 of the wall portion 2, the glass layer 6 and the adhesive 7 are also completely arranged around the through-hole 10 of the wall portion 2.

In summary, the device according to the invention has a simple construction type and very good sealing properties.

The device 1 is particularly suited for monitoring the production of biomass in a bioreactor.

Different types of glass, which are preferably selected in accordance with the type of sensor and/or the intended use of the device, can be used for the glass layer 6. The glass layer 6 may, for example, substantially comprise quartz glass, also referred to as silica glass. The quartz glass has a high chemical resistance and is permeable to infrared (IR) radiation up to ultraviolet (UV) radiation. Quartz glass is particularly suitable for optical sensors that detect electromagnetic radiation in the UV range. Alternatively, the glass layer 6 may, for example, substantially comprise calcium fluoride. Calcium fluoride is also permeable to IR and UV radiation. Calcium fluoride is particularly suited to optical sensors that detect electromagnetic radiation in the IR range. In accordance with the initial material and production process, commercially available glass can have small quantities of impurities and/or additives that do not impair the significant properties of the glass. Therefore, it is sufficient for the glass to substantially comprise a specific type of glass.

In a preferred embodiment, the glass layer 6 is arranged facing the silanization layer 3. The adhesive 7 can thereby have a relatively great contact surface both with the glass layer 6 and with the silanization layer 3. The adhesive 7 thereby bonds the silanization layer 3 to the glass layer 6 in a particularly durable manner.

Figure 4A:
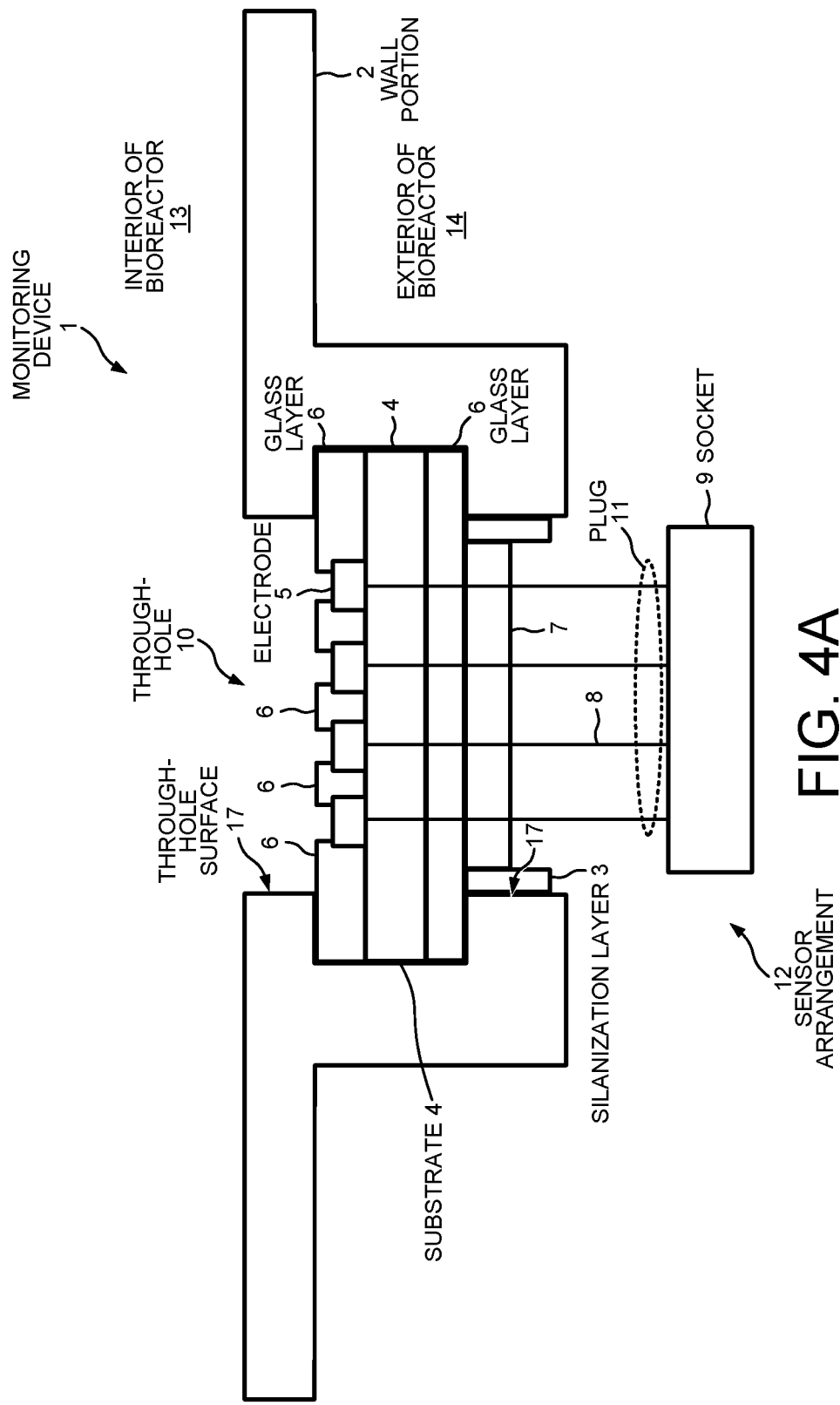
FIG. 4A is a schematic cross-section of an exemplary embodiment of the device according to the invention, wherein the wall portion has a through-hole surface which delimits the through-hole, and wherein the glass layer is further arranged between the electrodes and on a part-region on the surface of each electrode which faces away from the substrate, wherein the part-region completely contains the edge of the surface of each electrode facing away from the substrate.

FIG. 4A shows an alternative embodiment in which the wall portion 2 has a through-hole surface 17 that delimits the through-hole 10. The silanization layer 3 is applied to the through-hole 10 surface, and the sensor arrangement 12 is arranged in the through-hole 10. In this embodiment, the normal of the surface of the glass layer 6 is preferably arranged substantially perpendicularly to the normal of the surface of the silanization layer 3. This arrangement makes it easier to apply the adhesive 7 because the contact locations of the adhesive 7 with the glass layer 6 and the silanization layer 3 are readily accessible.

In a preferred embodiment, the adhesive 7 is a silicone adhesive or an epoxy resin adhesive. The inventors have found that the silicone adhesive or epoxy resin adhesive adhesively bonds the silanization layer 3 to the glass layer 6 in a particularly durable and particularly tight manner. Furthermore, these adhesives withstand a sterilization with gamma radiation.

The epoxy resin adhesive may include, for example, bisphenol A diglycidyl ether, bisphenol F diglycidyl ether, phenol novolacs, aliphatic epoxides and/or cycloaliphatic epoxides.

In a preferred embodiment, the epoxy resin adhesive is a two-component adhesive. In this case, the adhesive 7 has an epoxy resin and a curing agent. By mixing the epoxy resin with the curing agent directly before using the adhesive 7, the reaction by means of which the adhesive 7 is cured is started. The curing agent may be, for example, an amine.

The inventors have tested different commercially available silicone adhesives and epoxy resin adhesives. In this case, a particularly durable and good sealing action was achieved with the silicone adhesive RS692-542. Furthermore, a particularly durable and good sealing action was achieved with the epoxy resin adhesives Hysol RE2039 (epoxy resin) with Hysol HD6652 (curing agent), EPO-TEK 301, EPO-TEK 301-2, Polytec EP 601 and Aremco-Bond 2310.

In a preferred embodiment, the two-component adhesive is EPO-TEK 301. A particularly durable and good sealing action was also achieved here. In another embodiment, the two-component adhesive has Hysol RE2039 as the epoxy resin and Hysol HD6652 as the curing agent. A particularly durable and good sealing action was also achieved here.

In a preferred embodiment, the wall portion 2 is made of a plastic material or a glass. The walls of bioreactors are often comprised substantially of glass or plastic material. The wall portion 2 can be made of any material so long as it is possible to apply the silanization layer 3 directly to the material of the wall portion 2. Glass can be silanised readily and in a known manner. The application of the silanization layer 3 to the wall portion 2 can be carried out by direct silanization, as with glass, or by surface activation of the wall portion 2 with subsequent silanization, as is the case, for example, with plasma-silanization of plastic materials.

Disposable bioreactors are generally produced from plastic material. In a particularly preferred embodiment, the wall portion 2 therefore is made of plastic material. The wall portion 2 can thereby readily be welded to a wall of the disposable bioreactor of plastic material or even be a portion of the wall of the bioreactor.

In a further preferred embodiment, the plastic material has HDPE. The abbreviation "HDPE" refers to "high-density polyethylene". HDPE is also referred to as hard polyethylene (PE). HDPE has weakly branched polymer chains and therefore a high density. The density of HDPE is typically from 0.94 g/cm3 to 0.97 g/cm3.

In a preferred embodiment, the wall portion 2 is made of HDPE.

In a particularly preferred embodiment, the wall portion 2 is comprised substantially of HDPE. Commercially available HDPE may have small quantities of impurities and/or additives that do not impair the significant properties of the HDPE. Therefore, it is sufficient for the wall portion 2 to be comprised substantially of HDPE. Since HDPE can easily be welded, the wall portion 2 can readily be welded to the wall of the bioreactor, which is also made of a plastic material. In a particularly preferred embodiment, the wall portion 2 comprises HDPE.

In a preferred embodiment, the wall portion 2 includes HDPE, and the adhesive 7 is a silicone adhesive or an epoxy resin adhesive. The inventors have found that HDPE can be adhesively bonded to the glass layer 6 in a durable, long-lasting and tight manner by means of the silicone adhesive or epoxy resin adhesive after the silanization layer 3 is applied.

In a preferred embodiment, the wall portion 2 is a rigid component. The rigid component is preferably a plate, such as, for example, a connection plate that can be securely connected to the wall of the bioreactor. Alternatively, the rigid component may have a first portion and a second portion, wherein the first portion is configured to be securely connected to another portion of the wall of the bioreactor, and the second portion has the through-hole surface 17. The first portion and the second portion are preferably arranged substantially perpendicularly to each other. As a result of the rigid component, the device can be fitted in the bioreactor in a particularly stable manner. This is particularly advantageous in bioreactors, whose containers are made of flexible plastic material and which are moved during operation of the bioreactor in order to circulate the biomass.

In a preferred embodiment, the wall portion 2 is the rigid component that is made substantially of HDPE, and the adhesive 7 is a silicone adhesive or an epoxy resin adhesive.

The wall portion 2 can also be formed by the wall of the bioreactor. It is not thereby necessary to connect the wall portion 2 securely to the wall of the bioreactor, whereby the device has an even simpler construction type. This embodiment is conceivable in particular for bioreactors whose walls are made of rigid plastic material or a different rigid material.

In a preferred embodiment, the carrier includes the glass layer 6. The carrier provides an optical window in this case. This allows the use of sensor arrangements that have optical sensors.

In a preferred embodiment, the sensor arrangement 12 has an optical sensor that has a detector configured to detect electromagnetic radiation that strikes the detector via the through-hole 10 and the glass layer 6. The optical sensor can additionally have a radiation source, wherein the detector is configured to detect radiation emitted by the radiation source after the interaction thereof with the liquid medium. In this case, the light source and the detector can be arranged at the same side of the device or at opposite sides of the device.

In a preferred embodiment, the carrier has a substrate 4, to which the glass layer 6 is applied. The sensor arrangement 12 has at least one of the sensors, wherein the at least one sensor is arranged on the substrate 4. The glass layer 6 is applied directly to the substrate 4. The glass layer 6 can be arranged on the entire surface of the substrate 4 which faces the silanization layer 3. Alternatively, the glass layer 6 may have recesses so that there is a region free from the glass layer 6 on the substrate 4. The sensor is preferably arranged on a region of the substrate 4 free from the glass layer 6. Additionally or alternatively, it is conceivable for the sensor to be arranged on a region of the substrate 4 free from the glass layer 6, and for the glass layer 6 to be further arranged on a part-region on the surface of the sensor facing away from the substrate 4.

In a preferred embodiment, the substrate 4 is a ceramic material substrate, wherein the ceramic material substrate preferably includes silicon oxide and/or aluminum oxide. In a particularly preferred embodiment, the ceramic material substrate is comprised of silicon oxide and/or aluminum oxide.

In a preferred embodiment, the sensor arrangement 12 has a conductivity sensor, wherein the conductivity sensor has at least two electrodes 5. The conductivity sensor is configured to measure the electrical conductivity between the two electrodes. The electrodes 5 are applied to the substrate 4. The sensor arrangement 12 may further have discharge tracks that are connected in an electrically conductive manner to the electrodes and which are guided through the carrier via through-connection locations. Furthermore, the sensor arrangement 12 may have contact locations that are connected in an electrically conductive manner to the discharge tracks and that are provided to be connected to an electronic measuring unit 19 in an electrically conductive manner. The sensor arrangement 12 may further have a plastic member that holds the discharge tracks of the electrodes 5 together.

In a preferred embodiment, the glass layer 6 is further arranged between the electrodes and the substrate 4. By the glass layer 6 also being arranged between the electrodes 5 and the substrate 4, the glass layer 6 further provides a seal between the electrodes 5 and the substrate 4. In particular, the through-connection locations in the substrate 4 are thereby sealed.

In an alternative embodiment, the electrodes 5 are applied to the substrate 4, and the glass layer 6 is further arranged between the electrodes 5 and on a part-region on the surface of each electrode facing away from the substrate 4. The part-region completely contains the edge of the surface of each electrode 5 facing away from the substrate 4. The term "part-region" as used here is intended to be understood to mean the region of the surface of an electrode 5 facing away from the substrate 4, which region is covered by the glass layer 6. In this embodiment, the glass layer 6 also provides a seal between the electrodes and the substrate 4. In particular, the through-connection locations in the substrate 4 are thereby sealed.

In a preferred embodiment, the electrodes 5 are applied to the substrate 4 by means of thin-film technology or thick-film technology.

In a preferred embodiment, the sensor arrangement 12 has a conductivity sensor, wherein the conductivity sensor preferably has at least two electrodes 5, more preferably at least four electrodes. The electrodes 5 can, for example, be applied to the glass layer 6. The electrodes are connected to discharge tracks and contact locations for connecting the electronic measuring unit 19 on the rear of the glass layer 6 via through-connection locations in the glass layer 6. The sensor arrangement 12 can further have a plastics member that holds the discharge tracks of the electrodes together.

The electrodes 5 can be used, for example, for measuring conductivity, measuring electrochemical/capacitive biomass or cell density or measuring impedance.

The electrodes 5 may be, for example, metal electrodes, hydrogen electrodes or electrodes comprising graphite. In a preferred embodiment, the electrodes 5 are metal electrodes, preferably platinum electrodes.

In a preferred embodiment, the sensor arrangement 12 has a combination of different sensors. The device 1 is thereby suitable for monitoring a plurality of different parameters. The sensor arrangement 12 may, for example, have an optical sensor, an electrical conductivity sensor, a temperature sensor, an oxygen sensor and/or a pH value sensor.

In a preferred embodiment, the sensor arrangement 12 has a plug 11 and/or a socket 9, wherein one of the plug 11 and the socket 9 can be releasably connected to another of the plug and the socket. The sensor arrangement 12 can further have the electronic measuring unit 19 and the other of the plug 11 and the socket 9 that is connected to the electronic measuring unit 19 in an electrically conductive manner. In this case, an electrically conductive connection of the electronic measuring unit 19 to the sensor, in particular to the electrodes 5, exists in the connected state via the plug 11 and the socket 9. The electrically conductive connection allows the electronic measuring unit 19 to be connected to the sensor arrangement 12 in order to output the parameters detected by the sensors. By providing the plug 11 and the socket 9, the electronic measuring unit 19 and the other one of the plug 11 and the socket 9 can be re-used.

In a second aspect, the invention relates to a bioreactor having the device 1 and a container, in which the liquid medium is intended to be disposed during operation of the bioreactor. The container includes the wall portion 2, and the biological process is intended to be carried out during bioreactor operation. The container includes the wall of the bioreactor.

In a preferred embodiment, the carrier is fitted to a side of the wall portion 2 facing the exterior of the container. The device 1 can be readily fitted to the bioreactor in this manner.

In a preferred embodiment, the carrier is fitted to a side of the wall portion 2 facing the interior of the container. In this manner, the carrier provides more surface-area for fitting the sensor or a plurality of sensors. The sensor can be fitted to the entire side of the carrier facing the interior of the container. If the carrier is fitted to a side of the wall portion 2 facing the exterior of the container, however, the sensor can be fitted only on the portion of the carrier that is arranged directly at the through-hole 10.

In a preferred embodiment, the wall portion 2 is a rigid component. The rigid component is preferably a plate, such as, for example, a connection plate that is securely connected to another portion of the wall of the bioreactor. Alternatively, the rigid component has a first portion and a second portion, wherein the first portion is configured to be securely connected to another portion of the wall of the bioreactor, and the second portion has the through-hole surface. The first portion and the second portion are preferably arranged substantially perpendicularly to each other. As a result of the rigid component, the device can be fitted in the bioreactor in a particularly stable manner. This is advantageous in a container that is made substantially of a flexible plastic material because such a bioreactor is moved during bioreactor operation in order to circulate the biomass.

In a preferred embodiment, the container includes a plastic bag that is preferably flexible. The plastic bag has an additional through-hole 10 that corresponds to the through-hole 10 of the wall portion 2.

The plastic bag may be made of polyethylene terephthalate (PET), low-density polyethylene (LDPE), polyvinyl acetate (PVA), polyvinyl chloride (PVC) and/or polypropylene (PP).

In a preferred embodiment, the wall portion 2 is a rigid component, and the container is a plastic bag that is securely connected to the rigid component, wherein the plastic bag is preferably flexible. The secure connection between the plastic bag and the rigid component can be achieved, for example, by welding the plastic bag to the rigid component. The combination of a flexible plastic bag with a rigid component as a wall portion 2 is particularly advantageous. The device 1 is thereby secured in the bioreactor in a stable manner so that it can withstand the movements of the bioreactor during operation of the bioreactor.

In a preferred embodiment, the bioreactor is a disposable bioreactor. Disposable bioreactors have the advantage that complex cleaning and sterilization processes, which would be necessary before repeatedly operating the bioreactor, can be dispensed with. The disposable bioreactor can thereby also have materials that would not withstand such cleaning and sterilization processes.

In a third aspect, the invention relates to a method for producing a device for monitoring a biological process in a liquid medium, the method comprising the steps of:

a) providing a wall portion 2 that is configured to retain the liquid medium during operation of the device, and a silanization layer 3, wherein the wall portion 2 has a through-hole 10 and the silanization layer 3 is applied directly to the wall portion 2 and completely around the through-hole 10, b) providing a sensor arrangement 12, wherein the sensor arrangement 12 has a carrier that includes a glass layer 6, c) tightly bonding the silanization layer 3 to the glass layer 6 by means of an adhesive 7, and d) curing the adhesive 7.

For adhesively bonding the silanization layer 3 to the glass layer 6, it is advantageous to arrange the wall portion 2 relative to the sensor arrangement 12 in such a manner that the silanization layer 3 has spatial proximity to the glass layer 6.

Because the silanization layer 3 is arranged completely around the through-hole 10 of the wall portion 2, the adhesive-bonding of the silanization layer 3 to the glass layer 6 is also carried out completely around the through-hole 10 of the wall portion 2.

In a preferred embodiment, the adhesive 7 is a silicone adhesive or an epoxy resin adhesive.

In a preferred embodiment, the epoxy resin adhesive is a two-component adhesive.

The inventors have tested different commercially available silicone adhesives and epoxy resin adhesives. For example, the silicone adhesive RS692-542 has been found to be particularly suitable in this case. Furthermore, the epoxy resin adhesives Hysol RE2039 (epoxy resin) with Hysol HD6652 (curing agent), EPO-TEK 301, EPO-TEK 301-2, Polytec EP 601 and Aremco-Bond 2310 have been found to be particularly suitable.

In a preferred embodiment, the two-component adhesive is EPO-TEK 301.

In another embodiment, the two-component adhesive has Hysol RE2039 as the epoxy resin and Hysol HD6652 as the curing agent.

In a preferred embodiment, the wall portion 2 is made of a plastic material or a glass, preferably a plastic material, more preferably HDPE.

In a preferred embodiment, in step a) the silanization layer 3 is applied to the wall portion 2 by silanization with a silanization reagent. The silanization may be a direct silanization or a silanization after preceding surface activation of the wall portion 2, for example, by plasma activation. HDPE and other plastic materials can be silanised, for example, after a surface activation by means of plasma (plasma activation). The term "plasma activation" as used here is intended to be understood to refer to a method in which OH groups are incorporated in the surface of a plastic material by means of plasma. The OH groups react during the silanization with the silanization reagent. The term "plasma-silanization" as used here is intended to be understood to refer to a method for silanizing a surface in which initially an activation of the surface by means of plasma and subsequently a silanizing of the activated surface with a silanizing reagent is carried out. The plasma-silanization is used in particular in a wall portion 2 that is made of a plastic material.

Known silanizing reagents include, for example, 3-(triethoxysilyl)propyl isocyanate, methoxytrimethylsilane, ethoxytrimethylsilane, dimethoxydimethylsilane, trimethoxymethylsilane, trimethoxyethylsilane, trimethoxypropylsilane, trimethoxyphenylsilane, (trimethylsilyl)methanol, (trimethylsilyl)isocyanate, (3-aminopropyl) triethoxysilane, isopropoxytrimethylsilane and dimethoxy methyl phenylsilane. The silanizing reagent may also be an admixture of two or more compounds.

In a preferred embodiment, the silanizing reagent includes 3-(triethoxysilyl)propylisocyanate.

In a preferred embodiment, in step b) the glass layer 6 is applied by means of screen printing of a glass paste onto the carrier and is burnt in. By applying the glass paste, the through-connection locations in the carrier can be sealed at the same time.

In a preferred embodiment, before step c), before step d) or after step d) a plug 11 or a socket 9 is provided and securely connected to the wall portion 2. The secure connection between the plug 11 or the socket 9 and the wall portion 2 can be achieved, for example, by welding the plug or the socket to the wall portion.

The application of the adhesive 7 can be carried out, for example, by pouring or by applying the adhesive 7 by means of a template and a roller.

In a preferred embodiment, in step c) the adhesive 7 is applied to the silanization layer 3 and to the glass layer 6.

The curing of the adhesive 7 can be carried out, for example, at ambient temperature, that is to say, at approximately 23° C., or at a higher temperature. At higher temperatures, the duration of the curing operation is reduced, and a higher level of strength of the cured adhesive 7 is generally achieved.

In a preferred embodiment, step d) is carried out for 24 hours at approximately 23° C. or for 1 hour at 65° C.

The silicone adhesive RS692-542 is preferably cured at approximately 23° C.

The epoxy resin adhesives Hysol RE2039 (epoxy resin) with Hysol HD6652 (curing agent), EPO-TEK 301, EPO-TEK 301-2, Polytec EP 601 and Aremco-Bond 2310 are preferably cured at 65° C.

In a preferred embodiment, the two-component adhesive is EPO-TEK 301, and step d) is carried out for one hour at 65° C.

In another embodiment, the two-component adhesive has Hysol RE2039 as the epoxy resin and Hysol HD6652 as the curing agent and step d) is carried out for one hour at 65° C.

Figure 2A:
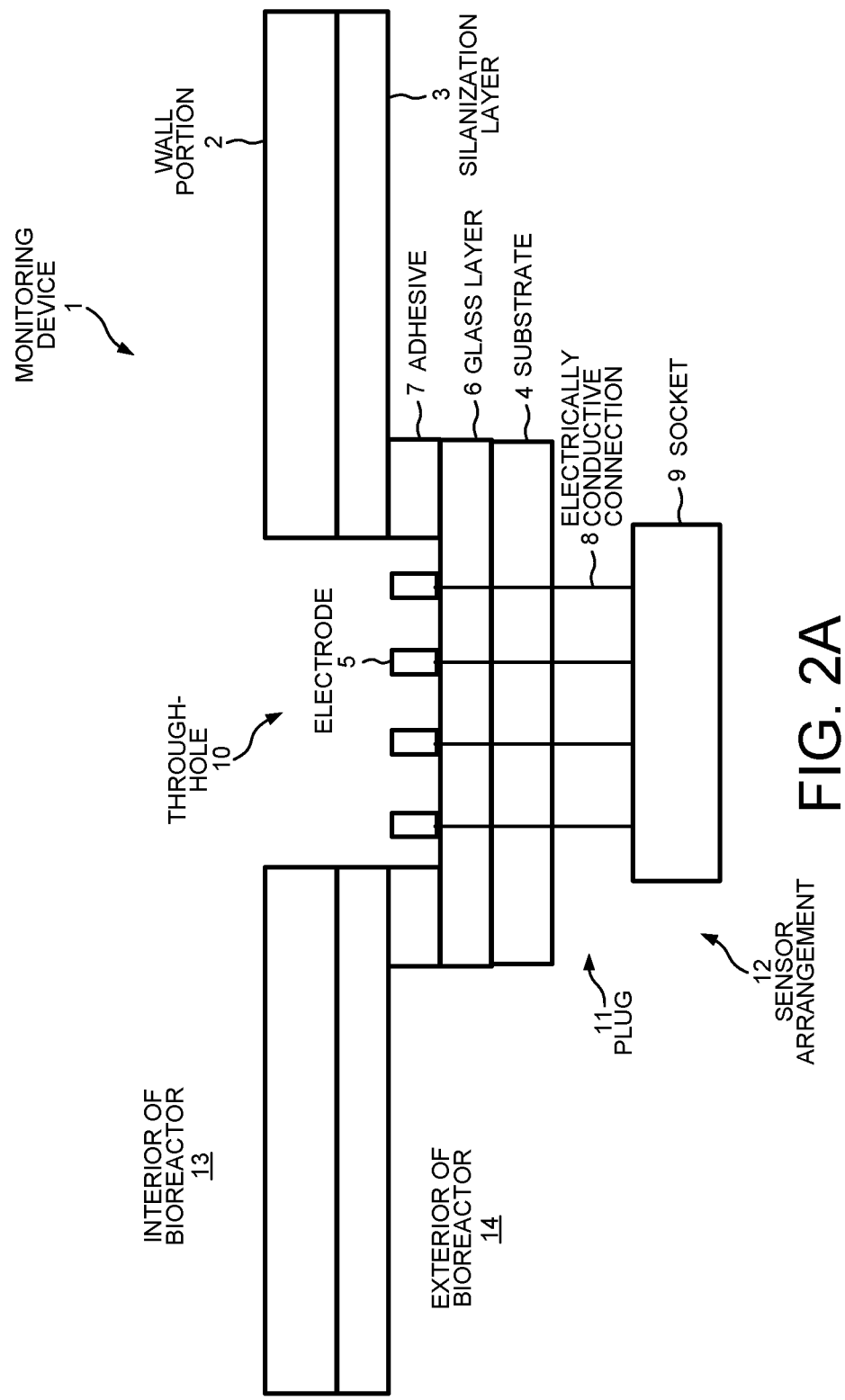
FIGS. 2A and 2B show schematic cross-sections of two exemplary embodiments of the device according to the invention, wherein the substrate is fitted to a side of the wall portion that faces the exterior of the bioreactor.
Figure 2B:
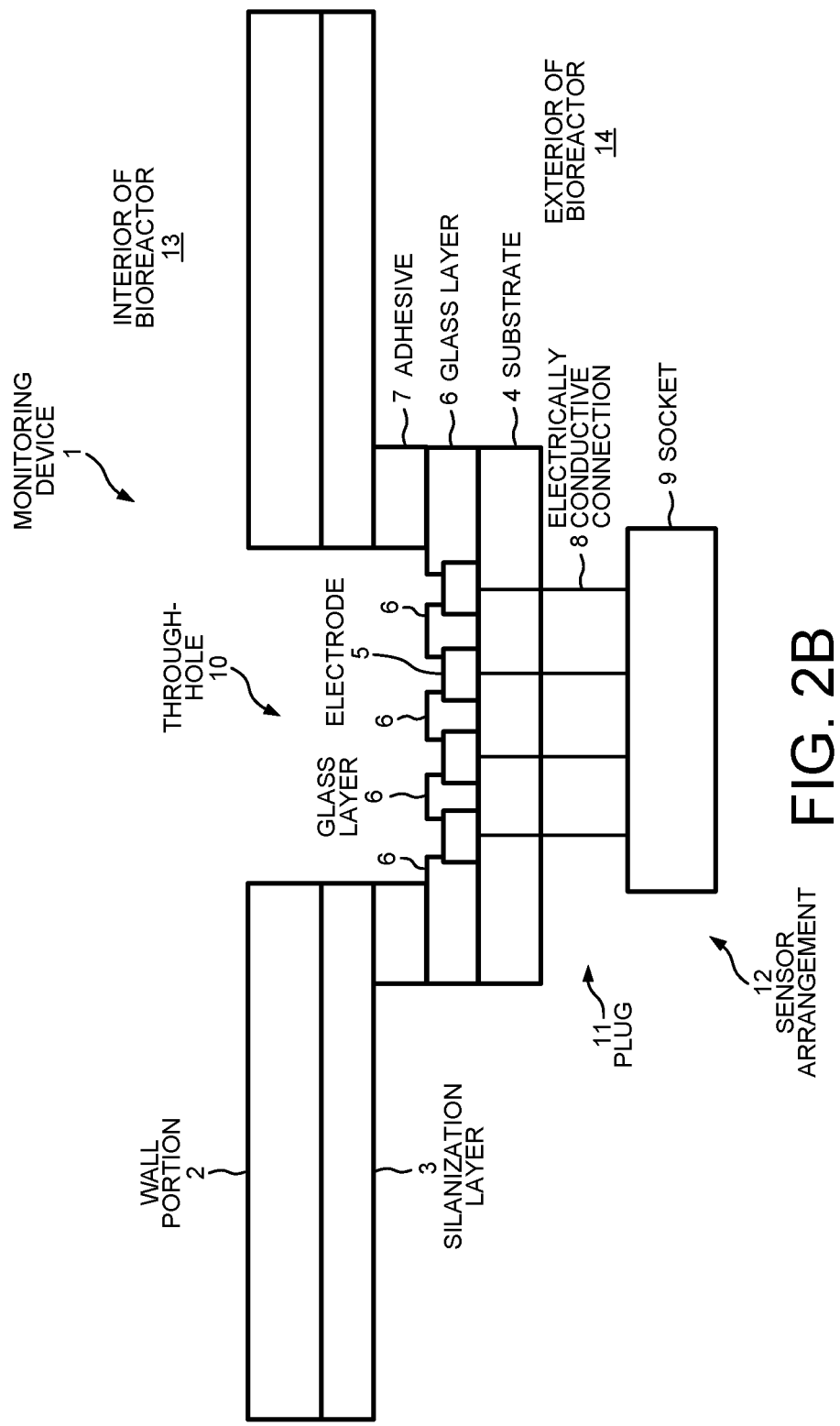

Each of FIGS. 1, 2A and 2B show a cross-section of a preferred embodiment of the device 1 according to the invention. As can be seen in FIGS. 1, 2A and 2B, the device 1 has the wall portion 2, the silanization layer 3, the adhesive 7, the glass layer 6, the substrate 4, four electrodes 5, four electrically conductive connections 8 and a socket 9. The substrate 4, the electrodes 5, the glass layer 6, the electrically conductive connections 8 and the socket 9 form portions of a sensor arrangement 12 of the device 1. The wall portion 2 is made of HDPE and has a through-hole 10. The silanization layer 3, the adhesive 7 and the glass layer 6 completely surround the through-hole 10. The silanization layer 3 is applied directly to the wall portion 2 and is bonded tightly to the glass layer 6 by means of the adhesive 7. The glass layer 6 is applied directly to the substrate 4. The substrate 4 is a ceramic material that includes silicon oxide. The electrodes 5 that form a sensor are applied to the substrate 4. The electrodes 5 are platinum electrodes. The electrodes 5 are connected to a socket 9 via electrically conductive connections 8. The electrically conductive connections 8 can be metal pins that form a plug 11. Alternatively, the electrically conductive connections 8 may be wires.

Alternatively, the glass layer 6 may be present without the substrate 4, wherein the electrodes 5 are arranged on the glass layer 6 in this case.

In FIG. 1, the substrate 4 is fitted to a side of the wall portion 2 facing the interior 13 of a bioreactor.

In FIGS. 2A and 2B, however, the substrate 4 is attached to a side of the wall portion 2 facing the exterior 14 of a bioreactor.

In FIG. 2A, the glass layer 6 is disposed between the electrodes 5 and the substrate 4. The electrodes 5 are free from the glass layer 6.

Unlike as in FIG. 2A, the glass layer 6 in FIG. 2B is arranged between the electrodes 5 and on the electrodes 5 in a region along the entire periphery of each electrode 5. The electrodes 5 are thereby partially covered by the glass layer 6. Each electrode 5 has at its centre a region free from the glass layer 6 so that the electrodes 5 can perform their function, for example, for measuring conductivity in the liquid medium.

Figure 3A:
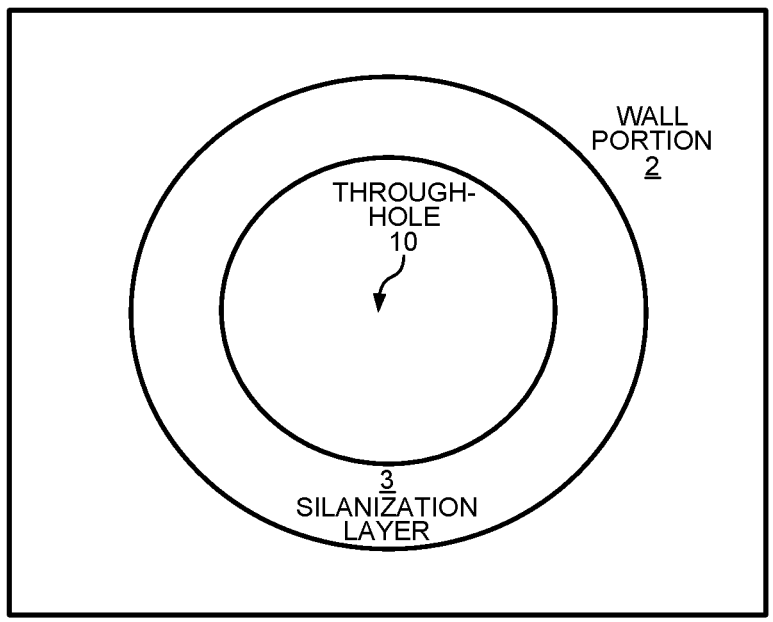
FIG. 3A is a schematic plan view of the wall portion of the inventive device.

FIG. 3A is a plan view of the wall portion 2. It can be seen that the wall portion 2 has a through-hole 10, and the silanization layer 3 is arranged completely around the through-hole 10.

Figure 3B:
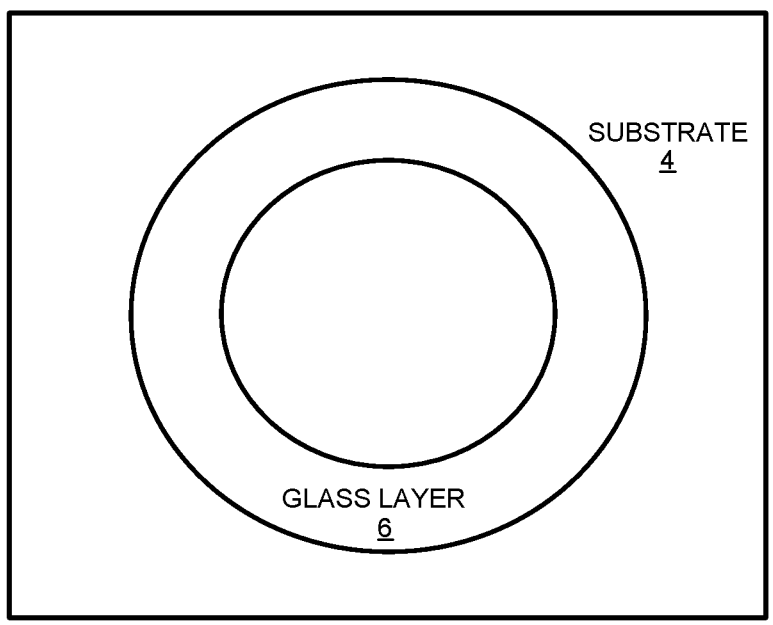
FIG. 3B is a schematic plan view of the substrate of the inventive device.

FIG. 3B is a plan view of the substrate 4. It can be seen that the glass layer 6 is arranged on the substrate 4 in a region that is arranged completely around the through-hole 10 in the assembled device 1. Alternatively, the glass layer 6 can be arranged on the entire surface of the substrate 4 that faces the silanization layer 3.

The embodiments of the device 1 shown in FIGS. 1, 2A and 2B can be produced as follows.

Initially, the wall portion 2 which comprises HDPE and which has a through-hole 10 is made. Then, the silanization layer 3 is applied directly to the wall portion 2 by plasma-silanizing. For the plasma-silanizing, two open glass containers are each filled with approximately 0.1 ml of 3-(triethoxysilyl)propyl isocyanate and placed, together with the wall portion 2, in a vacuum chamber of a so-called plasma-silanizing plant. In this case, the wall portion 2 is arranged between two electrodes in the vacuum chamber. The vacuum chamber is then evacuated down to approximately 0.2 mbar, and plasma is ignited by means of a generator between the two electrodes in the vacuum chamber. The wall portion 2 is processed and silanised for two minutes with plasma. Subsequently, the vacuum chamber is vented.

In the next step, the substrate 4 is made together with the electrodes 5, the glass layer 6 and the electrically conductive connections 8. Furthermore, the plug 11 is produced. The wall portion 2, the substrate 4 and the plug 11 are joined by placing the wall portion 2 on a table, then placing the substrate 4 thereon, and finally placing the plug 11 thereon. The plug 11 is then welded to the wall portion 2. The glass layer 6 of the substrate 4 and the silanization layer 3 of the wall portion 2 are not securely connected to each other in this case. The substrate 4 can in particular still be moved. The substrate 4 is slightly lifted off the wall portion 2 in order to apply the adhesive 7 to the glass layer 6 and the silanization layer 3. After the adhesive 7 has been applied, the substrate 4 and the wall portion 2 are positioned relative to each other so that the adhesive 7 bonds the silanization layer 3 to the glass layer 6. Finally, the adhesive 7 is cured at 65° C. for one hour.

FIG. 4A shows a cross-section of a preferred embodiment of the device 1. The device 1 has a wall portion 2, a silanization layer 3, an adhesive 7, a glass layer 6, a substrate 4, a plurality of electrodes 5, a plurality of electrically conductive connections 8 and a socket 9. The device 1 can, for example, have four electrodes 5 and four electrically conductive connections 8. The wall portion 2 is made of HDPE and has a through-hole 10. It can be seen that the wall portion 2 has a through-hole surface 17 which delimits the through-hole 10. The substrate 4, the electrodes 5, the glass layer 6, the electrically conductive connections 8 and the socket 9 form portions of a sensor arrangement 12 of the device 1. The sensor arrangement 12 is arranged in the through-hole 10. The sensor arrangement 12 is fixed in the wall portion 2 by a peripheral groove in the wall portion 2. The sensor arrangement 12 cannot thereby be moved relative to the wall portion 2. The silanization layer 3 is applied directly to the through-hole surface 17 of the wall portion 2 and arranged completely around the through-hole 10. The glass layer 6 is applied directly to the substrate 4. The glass layer 6 is applied to the entire surface of the substrate 4 facing the exterior 14 of the bioreactor and further applied to the surface of the substrate 4 facing the interior 13 of the bioreactor.

Figure 6:
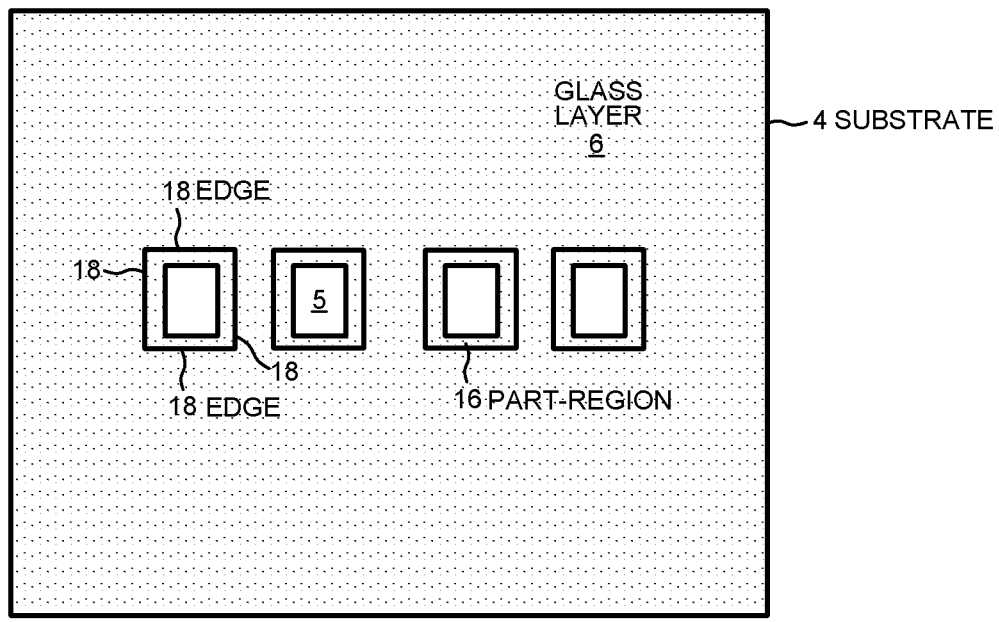
FIG. 6 is a schematic plan view of the substrate, on which the glass layer is arranged between the electrodes and on a part-region on the surface of each electrode that faces away from the substrate, wherein the part-region completely contains the edge of the surface of each electrode facing away from the substrate.

As shown in FIG. 6, at the surface of the substrate 4 facing the interior 13 of a bioreactor, the glass layer 6 is formed between the electrodes 5 and on a part-region 16 on the surface of each electrode 5 facing away from the substrate 4. The part-region 16 completely contains the edge 18 of the surface of each electrode 5 which faces away from the substrate 4. The electrodes 5 are thereby partially covered by the glass layer 6. A center region of the top surface of each electrode 5 is not covered by the glass layer 6. Thus, each electrode 5 has at the center thereof a region that is free from the glass layer 6 so that the electrodes 5 can perform their function, for example, for measuring conductivity.

Figure 5:
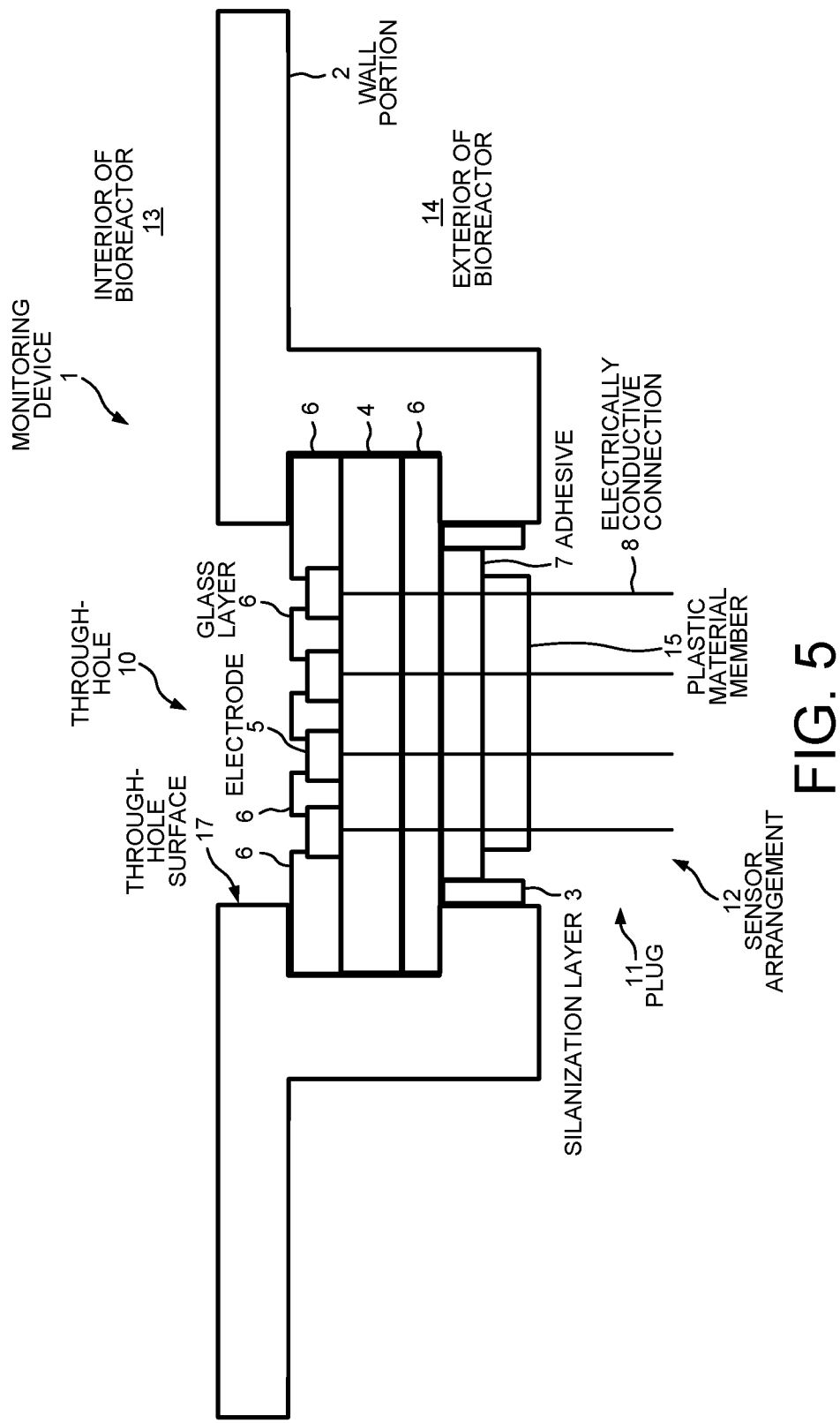
FIG. 5 is a schematic cross-section of an exemplary embodiment of the device according to the invention, wherein the sensor arrangement has a plastic material member that holds together the electrically conductive connections.

As shown in FIG. 5, the normal of the surface of the glass layer 6 facing the exterior 14 of a bioreactor is arranged perpendicularly to the normal of the surface of the silanization layer 3. The silanization layer 3 is bonded tightly by means of the adhesive 7 to the region of the glass layer 6 facing the exterior 14 of the bioreactor. The adhesive 7 is arranged completely around the through-hole 10. The adhesive 7 is applied to the entire region of the glass layer 6 facing the exterior 14 of a bioreactor. Alternatively, the adhesive 7 can be applied only in a portion of the region of the glass layer 6 facing the exterior 14 of the bioreactor such that the portion is arranged completely around the through-hole 10. The substrate 4 is a ceramic material substrate which contains silicon oxide. The electrodes 5, which form a sensor, are mounted to the substrate 4. The electrodes 5 may be, for example, platinum electrodes. The electrodes 5 are connected to a socket 9 via electrically conductive connections 8. The electrically conductive connections 8 may be metal pins that form a plug 11. Alternatively, the electrically conductive connections 8 may be wires.

The embodiment of the device 1 as shown in FIG. 4A can be produced as follows.

Figure 4B:
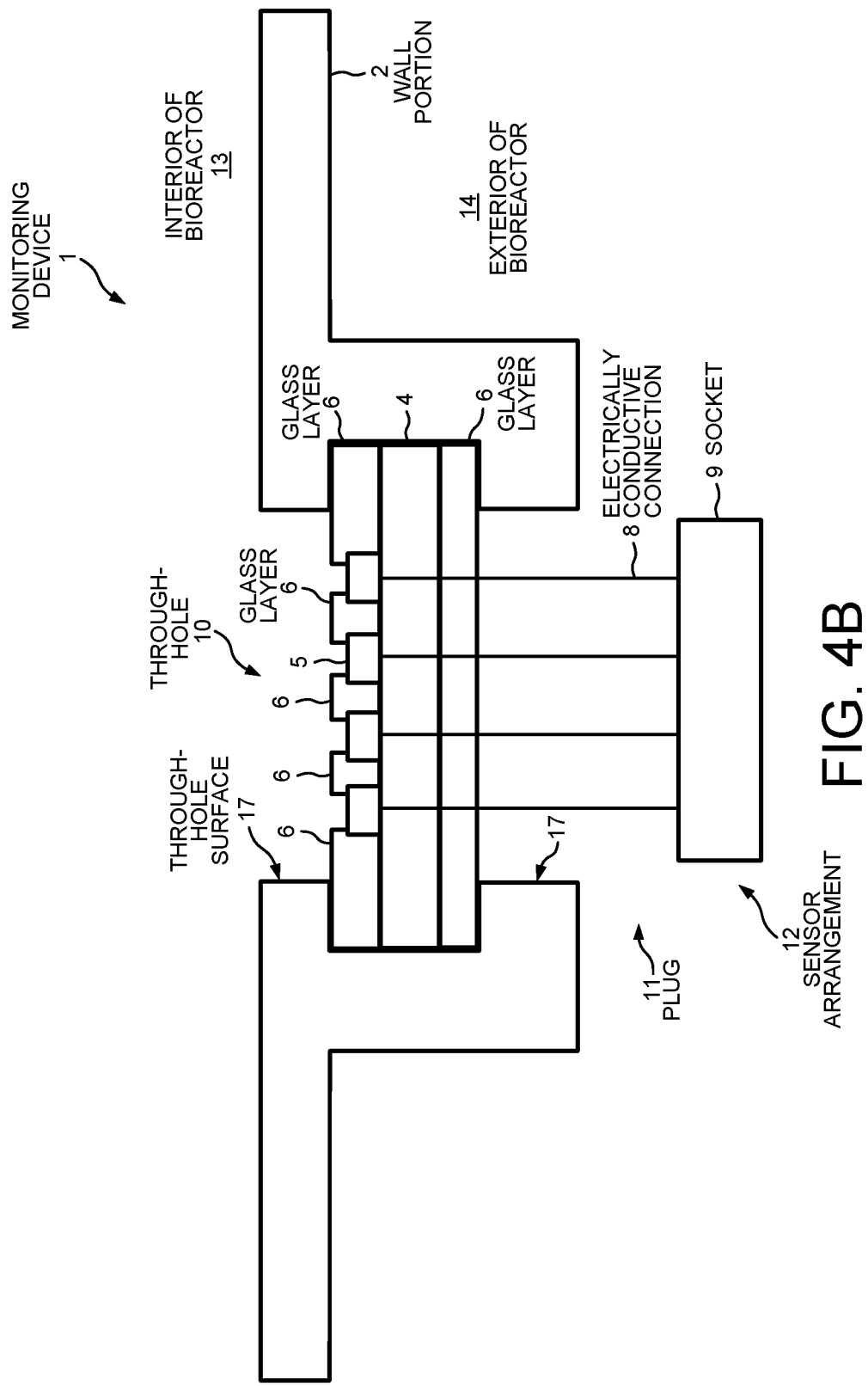
FIG. 4B shows an intermediate product of the production of the embodiment of FIG. 4A.

Initially, the substrate 4 is provided with the electrodes 5, the glass layer 6 and the electrically conductive connections 8. The substrate 4 is placed in an injection-molding device. The injection-molding device determines the dimensions of the wall portion 2. The substrate 4 is arranged in the injection-molding device in such a manner that it will be positioned in the through-hole 10 of the wall portion 2. HDPE is injected around the substrate 4 in flowable form into the injection-molding device along the periphery of the substrate 4 and cured by cooling. The cured HDPE forms the wall portion 2 which has a through-hole surface 17 and that is securely and tightly connected to the substrate 4 by the injection-molding step. FIG. 4B shows the wall portion 2 that is connected to the substrate 4.

In the next step, the silanization layer 3 is directly applied by plasma-silanizing to the through-hole surface 17 of the wall portion 2. The silanization layer 3 is applied to a region of the through-hole surface 17 facing the exterior 14 of the bioreactor. The silanization step is carried out substantially as described for the embodiments of the device 1 as shown in FIGS. 1, 2A and 2B.

In the next step, the application of the adhesive 7 is carried out. To this end, the wall portion 2 connected to the substrate 4 is placed on a table on the side thereof facing the interior 13 of the bioreactor. The adhesive 7 is applied from the side of the substrate 4 facing the exterior 14 of the bioreactor beside the electrically conductive connections 8. As a result of the application and/or gravitational force, the adhesive 7 reaches the glass layer 6 and the silanization layer 3. In this case, only so much adhesive 7 is applied so that the ends of the electrically conductive connections 8 facing the exterior 14 of the bioreactor are not covered by adhesive 7. The adhesive 7 bonds the silanization layer 3 to the glass layer 6. The device 1 is thereby additionally sealed. Finally, the adhesive 7 is cured at 65° C. for one hour.

Alternatively, the substrate 4 can be provided in the first step with the electrodes 5 and the glass layer 6, but without the electrically conductive connections 8. In this case, the electrically conductive connections 8 are fitted to the electrodes 5 before the adhesive 7 is applied, that is to say, after the injection-molding step or after the silanizing step. The electrically conductive connections 8 are attached by soldering.

FIG. 5 is a cross-section of a preferred embodiment of the device 1. FIG. 5 substantially corresponds to the embodiment shown in FIG. 4A, wherein the socket 9 is not shown. It can be seen that the sensor arrangement 12 of the device 1 has a plastic material member 15. The plastic material member 15 holds together the electrically conductive connections 8. The adhesive 7 is applied as far as the surface of the plastic material member 15 which faces the glass layer 6.

FIG. 6 is a plan view of the surface of the substrate 4 facing the interior 13 of the bioreactor. The substrate 4 substantially corresponds to the substrate 4 of the embodiments of the device 1 as shown in FIGS. 2B, 4A and 5. The electrodes 5 that form a sensor are applied to the substrate 4. The glass layer 6 is formed on the substrate 4 between the electrodes 5. It can be seen that the glass layer 6 is additionally disposed on a part-region 16 on the surface of each electrode 5 facing away from the substrate 4 such that the part-region 16 completely contains the edge 18 of the surface of each electrode 5 facing away from the substrate 4. Each electrode 5 thereby has a part-region 16 that is covered by the glass layer 6. Each electrode 5 has at its top center a region free from the glass layer 6 so that the electrodes 5 can perform their function, for example, measuring conductivity through the liquid medium.

Figure 7A:
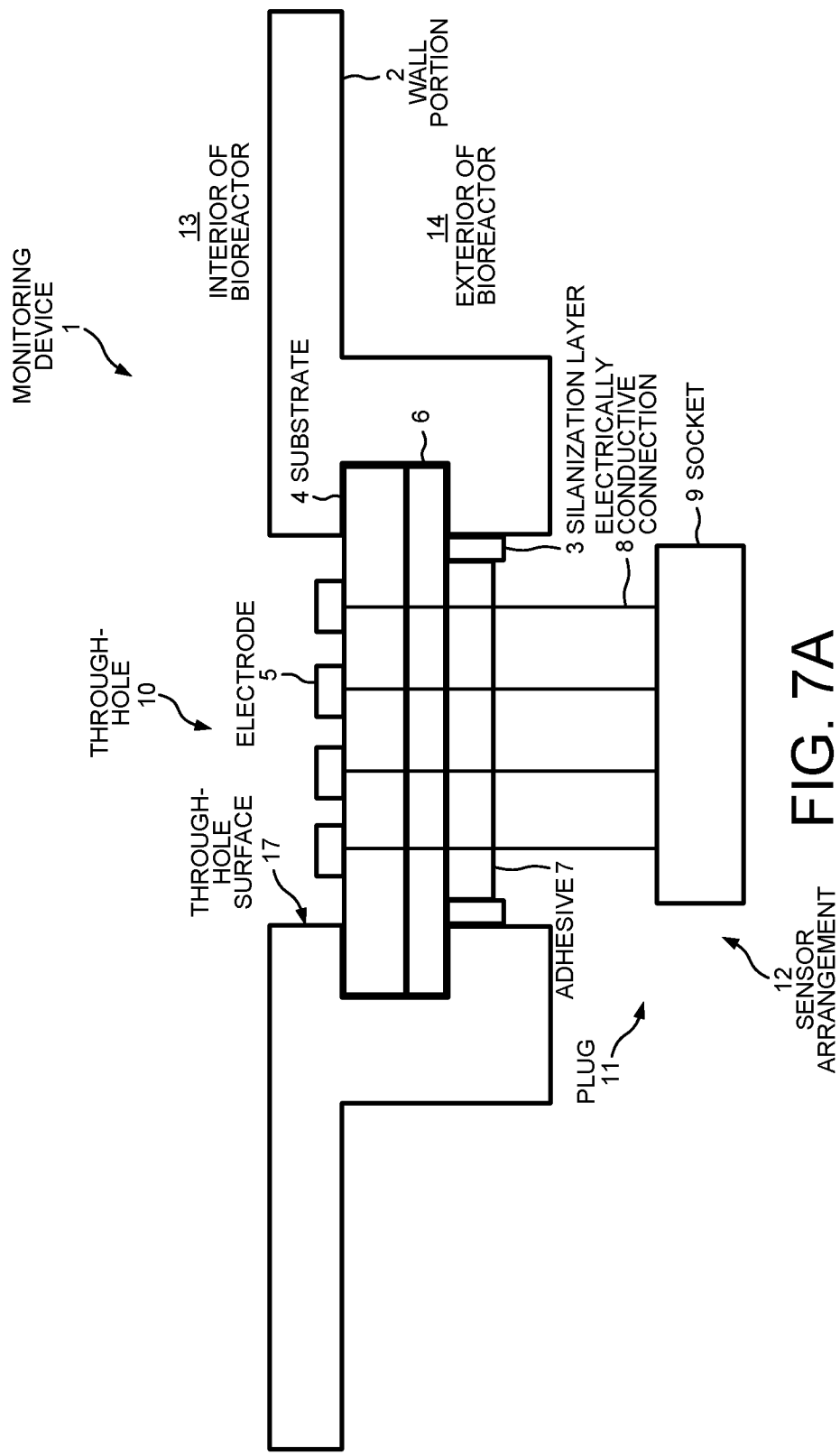
FIG. 7A is a schematic cross-section of an exemplary embodiment of the device according to the invention, wherein the wall portion has a through-hole surface that delimits the through-hole, and wherein the glass layer is applied exclusively to the surface of the substrate that faces the exterior of a bioreactor.

FIG. 7A is a cross-section of a preferred embodiment of the device 1. FIG. 7A substantially corresponds to the embodiment shown in FIG. 4A. The difference is that, in the embodiment shown in FIG. 7A, the glass layer 6 is applied exclusively to the surface of the substrate 4 facing the exterior 14 of the bioreactor.

Figure 7B:
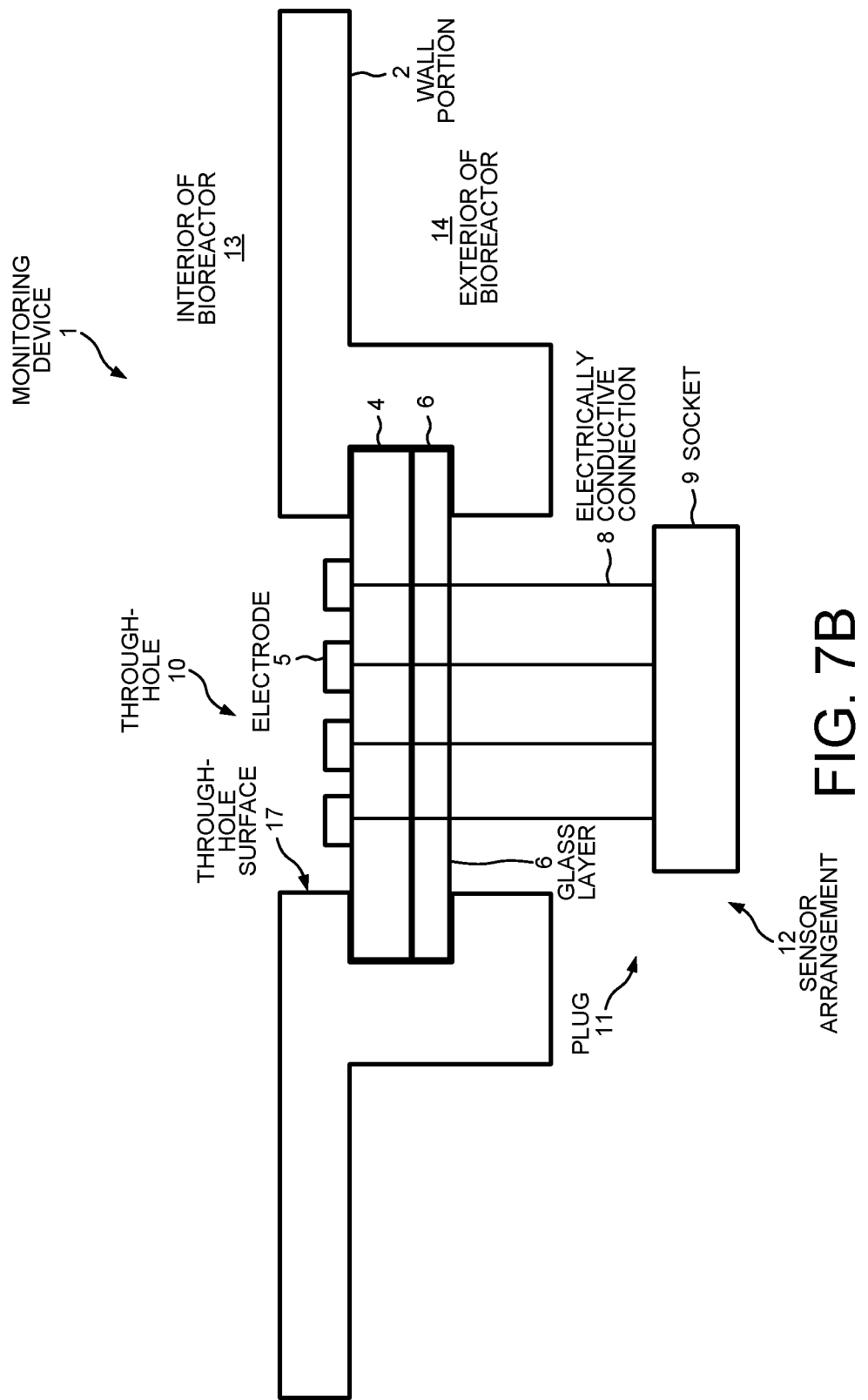
FIG. 7B shows an intermediate product of the production of the embodiment of the device of FIG. 7A.

The embodiment of the device 1 as shown in FIG. 7A can be produced as described for the embodiment shown in FIG. 4A. FIG. 7B shows the wall portion 2 connected to the substrate 4.

REFERENCE NUMERALS 1 monitoring device
2 wall portion
3 silanization layer
4 substrate
5 electrodes
6 glass layer
7 adhesive
8 electrically conductive connection
9 socket
10 through-hole
11 plug
12 sensor arrangement
13 interior of container
14 exterior of container
15 plastic material member
16 part-region of electrode
17 through-hole surface
18 edge of surface of electrode
19 electronic measuring unit Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A device for monitoring a biological process in a liquid medium, comprising:
a wall portion that is adapted to retain the liquid medium during operation of the device, wherein a through-hole is disposed in the wall portion;
a silanization layer disposed on the wall portion between the liquid medium and the wall portion;
a sensor arrangement that includes a glass layer; and
an adhesive that bonds the glass layer to the silanization layer such that the glass layer covers the through-hole.

2. The device of claim 1, wherein the wall portion has a through-hole surface encircling the through-hole, wherein the silanization layer covers the through-hole surface, and wherein the sensor arrangement is disposed adjacent to the through-hole.

3. The device of claim 2, wherein the through-hole surface that is covered by the silanization layer is oriented substantially perpendicularly to the glass layer.

4. The device of claim 1, wherein the adhesive is selected from the group consisting of: a silicone adhesive and a two-component epoxy resin adhesive.

5. The device of claim 1, wherein the wall portion is made of high-density polyethylene (HDPE).

6. The device of claim 1, wherein the device is attached to a container of a bioreactor, wherein the container is made of a flexible material, and wherein the wall portion is rigid.

7. The device of claim 1, wherein the sensor arrangement has an optical sensor adapted to detect electromagnetic radiation that passes from the liquid medium through the glass layer.

8. The device of claim 1, wherein the sensor arrangement also includes a substrate disposed adjacent to the glass layer, and wherein a sensor is mounted to the substrate.

9. The device of claim 8, wherein the sensor includes an electrode adapted to measure electrical conductivity through the liquid medium.

10. The device of claim 1, wherein the sensor arrangement includes a substrate disposed adjacent to the glass layer, wherein an electrode is attached to the glass layer, and wherein the glass layer is disposed between the electrode and the substrate.

11. The device of claim 1, wherein the sensor arrangement includes a substrate disposed adjacent to the glass layer, wherein a first electrode and a second electrode are mounted to the substrate, and wherein a portion of the glass layer is disposed on the substrate between the first electrode and the second electrode.

12. The device of claim 11, wherein the first and second electrodes have bottoms attached to the substrate, top surfaces opposite the bottoms, and side surfaces between the bottoms and the top surfaces, and wherein the side surfaces of the first and second electrodes are completely covered by the glass layer.

13. The device of claim 12, wherein only a center region of each of the top surfaces of the first and second electrodes is not covered by the glass layer.

14. The device of claim 11, wherein the sensor arrangement is adapted to sense electrical conductivity through the liquid medium between the first electrode and the second electrode.

15. A bioreactor comprising:
a container adapted to retain a liquid medium in an interior of the bioreactor;
a wall portion of a monitoring device, wherein the wall portion forms part of the container, and wherein a through-hole is disposed in the wall portion; and
a sensor arrangement of the monitoring device, wherein the sensor arrangement includes a substrate, a glass layer and an electrode, wherein the electrode is mounted on the substrate, wherein the substrate is disposed between the electrode and the glass layer, wherein the glass layer is attached to the wall portion such that the glass layer covers the through-hole, and wherein the electrode is disposed in the interior of the bioreactor.

16. The bioreactor of claim 15, wherein the wall portion has a through-hole surface encircling the through-hole, wherein a silanization layer covers the through-hole surface, and wherein the glass layer is bonded to the silanization layer.

17. The bioreactor of claim 16, wherein the silanization layer covers the wall portion between the liquid medium and the wall portion.

18. The bioreactor of claim 15, wherein the container is made of a flexible material, wherein the wall portion is rigid, and wherein the flexible container is attached to the rigid wall portion.

19. The bioreactor of claim 15, wherein the bioreactor is disposable.

20. The bioreactor of claim 15, wherein the sensor arrangement includes an optical sensor adapted to detect electromagnetic radiation that passes from the liquid medium through the glass layer.

21. The bioreactor of claim 15, wherein the electrode is adapted to measure electrical conductivity through the liquid medium.

22. The bioreactor of claim 15, wherein the glass layer is attached to the wall portion using an adhesive selected from the group consisting of: a silicone adhesive and a two-component epoxy resin adhesive.

23. The bioreactor of claim 15, wherein the electrode has a bottom that is attached to the substrate, a top surface opposite the bottom, and side surfaces between the bottom and the top surface, and wherein the side surfaces of the electrode are completely covered by glass of a second glass layer.

* * * * *